(12) United States Patent
Miller et al.

(10) Patent No.: US 11,081,227 B2
(45) Date of Patent: Aug. 3, 2021

(54) MONITORING AND REPORTING THE HEALTH CONDITION OF A TELEVISION USER

(71) Applicant: Sony Corporation, Tokyo (JP)

(72) Inventors: Lindsay Miller, San Diego, CA (US); Hyehoon Yi, San Diego, CA (US); Marvin DeMerchant, San Diego, CA (US)

(73) Assignee: Sony Corporation, Tokyo (JP)

( * ) Notice: Subject to any disclaimer, the term of this patent is extended or adjusted under 35 U.S.C. 154(b) by 284 days.

(21) Appl. No.: 16/054,520

(22) Filed: Aug. 3, 2018

(65) Prior Publication Data

US 2020/0043594 A1 Feb. 6, 2020

(51) Int. Cl.
*G16H 20/60* (2018.01)
*A61B 5/00* (2006.01)
(Continued)

(52) U.S. Cl.
CPC .......... *G16H 20/60* (2018.01); *A61B 5/6897* (2013.01); *G06T 15/08* (2013.01); *A61B 5/0205* (2013.01);
(Continued)

(58) Field of Classification Search
CPC ...... G16H 20/60; G16H 30/40; A61B 5/6897; A61B 5/0205; A61B 5/4803; A61B 5/486;
(Continued)

(56) References Cited

U.S. PATENT DOCUMENTS 6,478,736 B1 * 11/2002 Mault .................... A61B 5/083
600/300
8,644,754 B2 2/2014 Brown
(Continued)

FOREIGN PATENT DOCUMENTS

CN 107 566 908 1/2018
WO WO2014062032 4/2014

OTHER PUBLICATIONS

"Is your TV spying on You? It sounds like science fiction but many new TVs can watch you—telling advertisers your favourite shows or even filming you on the sofa. And there's no off switch!"; http://www.dailymail.co.uk/sciencetech/article-2513592/Is-TV-spying-YOU.html#ixzz58NoivZf3; Guy Adams for the Daily Mail; Nov. 26, 2013.

(Continued)

*Primary Examiner* — Malina D. Blaise
(74) *Attorney, Agent, or Firm* — Trellis IP Law Group, PC (57) ABSTRACT

Implementations generally relate to monitoring the health condition of a television user. In some implementations, a method includes detecting one or more activities of a user, wherein the one or more activities include watching television. The method further includes monitoring one or more health vitals of the user. The method further includes tracking a health status of the user based on the one or more activities and based on the monitoring of the one or more health vitals. The method further includes detecting one or more health anomalies based the health status. The method further includes responding to the one or more health anomalies based on one or more predetermined policies.

17 Claims, 6 Drawing Sheets

(51) Int. Cl.
*G06T 15/08* (2011.01)
*G16H 30/40* (2018.01)
*A61B 5/0205* (2006.01)
*G06K 9/00* (2006.01)
*H04N 21/422* (2011.01)
*H04N 21/4223* (2011.01)

(52) U.S. Cl.
CPC .............. *A61B 5/4803* (2013.01); *A61B 5/486* (2013.01); *A61B 5/4866* (2013.01); *A61B 5/742* (2013.01); *G06K 9/00228* (2013.01); *G06K 2209/17* (2013.01); *G16H 30/40* (2018.01); *H04N 21/4223* (2013.01); *H04N 21/42201* (2013.01); *H04N 21/42203* (2013.01)

(58) Field of Classification Search
CPC ....... A61B 5/4866; A61B 5/742; G06T 15/08; G06K 9/00228; G06K 2209/17; H04N 21/42201; H04N 21/42203; H04N 21/4223
See application file for complete search history.

(56) References Cited

U.S. PATENT DOCUMENTS

| | | | |
|---|---|---|---|
| 9,055,861 B2 | 6/2015 | Oh et al. | |
| 9,165,398 B2 | 10/2015 | Kim et al. | |
| 9,730,647 B2 | 8/2017 | Eyring | |
| 2002/0062069 A1* | 5/2002 | Mault | A61B 5/4872 600/300 |
| 2002/0107433 A1* | 8/2002 | Mault | A61B 5/1112 600/300 |
| 2003/0208110 A1 | 11/2003 | Mault | |
| 2011/0260830 A1 | 10/2011 | Weising | |
| 2012/0083705 A1* | 4/2012 | Yuen | G16H 20/30 600/508 |
| 2012/0095302 A1 | 4/2012 | Adhikari | |
| 2014/0081578 A1* | 3/2014 | Connor | G16H 20/60 702/19 |
| 2014/0156300 A1 | 6/2014 | Ohnemus et al. | |
| 2015/0164376 A1* | 6/2015 | Huang | A61B 5/6891 600/302 |
| 2015/0170542 A1* | 6/2015 | Contant | G16H 10/60 434/236 |
| 2016/0012749 A1 | 1/2016 | Connor | |
| 2016/0260352 A1 | 9/2016 | Ortiz | |
| 2016/0367193 A1* | 12/2016 | Zhang | A61B 5/02416 |
| 2017/0273629 A1* | 9/2017 | Yu | A61B 5/1176 |
| 2017/0287325 A1 | 10/2017 | Filatova et al. | |
| 2017/0329917 A1* | 11/2017 | Mcraith | G16H 10/60 |

OTHER PUBLICATIONS

SmartPLATE https://www.getsmartplate.com/—SmartPLATE Inc. "Year 2016http://ovens.reviewed.com/news/smartplate-tracks-what-you-eat-so-you-dont-have-to"; http://www.dailymail.co.uk/sciencetech/article-3068611/Easy-cheese-100-SmartPLATE-uses-hidden-camera-measure-perfect-portions-count-calories-you.html.
Samsung Smart TV http://www.dailymail.co.uk/sciencetech/article-2117493/Samsungs-latest-TV-sets-built-cameras-spark-concerns.html#ixzz58NtBiMJT—Samsung Electronics; Mar. 20, 2012.
Apple Patent Reveals Possible Future use of Biometrics for the Apple TV Remote that Works with HomeKit & more; http://www.patentlyapple.com/patently-apple/2017/09/apple-patent-reveals-possible-future-use-of-biometrics-for-the-apple-tv-remote-that-works-with-homekit-more.html; Patently Apple; Sep. 7, 2017.

* cited by examiner

MONITORING AND REPORTING THE HEALTH CONDITION OF A TELEVISION USER

BACKGROUND

More people are wearing or carrying devices to track biometric data for various applications. For example, people can carry phones and mobile fitness devices with biometric sensors that track heart rate and fitness level. Such devices can also track calories burned, number of steps taken, distances, etc. Some applications help people to track food. However, users need to take out their phones, open the selected applications, and manually enter information.

SUMMARY

Implementations generally relate to monitoring the health condition of a television user. In some implementations, a system includes one or more processors, and includes logic encoded in one or more non-transitory computer-readable storage media for execution by the one or more processors. When executed, the logic is operable to perform operations including detecting one or more activities of a user, wherein the one or more activities include watching a television; monitoring one or more health vitals of the user; tracking a health status of the user based on the one or more activities and based on the monitoring of the one or more health vitals; detecting one or more health anomalies based the health status; and responding to the one or more health anomalies based on one or more predetermined policies.

With further regard to the system, in some implementations, the system is in a fixed location. In some implementations, the system is associated with the television. In some implementations, the one or more activities include eating. In some implementations, the logic when executed is further operable to perform operations that comprise recognizing a type of food that the user is eating. In some implementations, the monitoring of the one or more health vitals is performed in association with a television remote control. In some implementations, at least one of the health vitals is heart rate.

In some embodiments, a non-transitory computer-readable storage medium with program instructions thereon is provided. When executed by one or more processors, the instructions are operable to perform operations including detecting one or more activities of a user, wherein the one or more activities include watching a television; monitoring one or more health vitals of the user; tracking a health status of the user based on the one or more activities and based on the monitoring of the one or more health vitals; detecting one or more health anomalies based the health status; and responding to the one or more health anomalies based on one or more predetermined policies.

With further regard to the computer-readable storage medium, in some implementations, the computer-readable storage medium is in a fixed location. In some implementations, the instructions are performed in association with the television. In some implementations, the one or more activities include eating. In some implementations, the instructions when executed are further operable to perform operations comprising recognizing a type of food that the user is eating. In some implementations, the monitoring of the one or more health vitals is performed in association with a television remote control. In some implementations, at least one of the health vitals is heart rate.

In some implementations, a method includes detecting one or more activities of a user, wherein the one or more activities include watching a television. The method further includes monitoring one or more health vitals of the user. The method further includes tracking a health status of the user based on the one or more activities and based on the monitoring of the one or more health vitals. The method further includes detecting one or more health anomalies based the health status. The method further includes responding to the one or more health anomalies based on one or more predetermined policies.

With further regard to the method, in some implementations, a system implementing the method is in a fixed location. In some implementations, the method is performed in associated with the television. In some implementations, the one or more activities include eating. In some implementations, the method further includes recognizing a type of food that the user is eating. In some implementations, the monitoring of the one or more health vitals is performed in association with a television remote control. In some implementations, at least one of the health vitals is heart rate.

A further understanding of the nature and the advantages of particular implementations disclosed herein may be realized by reference of the remaining portions of the specification and the attached drawings.

DETAILED DESCRIPTION

Implementations described herein monitor and report the health condition of a television user. In some implementations, a system detects one or more activities of a user (e.g., sitting, watching television, eating, etc.). People spend a significant number of hours sitting in front of a television (TV). They may have a hidden health problem or a diminishing health condition. The system monitors one or more health vitals of the user such as heart rate, etc. While sitting in front of the TV, they may behave in an unhealthy manner. For example, they may eat too much while watching a TV program. The system may also monitor the types of food a person eats while watching TV. The system further tracks the health status of the user based on the one or more activities and based on the monitoring of the one or more health vitals. The system further detects health anomalies based the health status, and responds to the health anomalies based on one or more predetermined policies.

Figure 1:
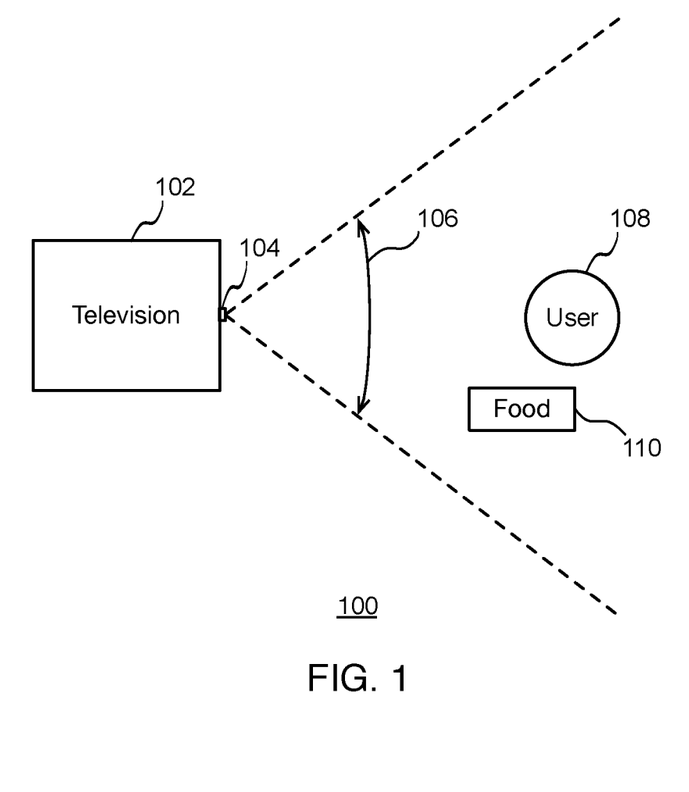
FIG. 1 illustrates a block diagram of an example television environment, which may be used for some implementations described herein.

FIG. 1 illustrates a block diagram of an example television environment 100, which may be used for some implementations described herein. In some implementations, television environment 100 includes a television 102, which includes a device 104. Device 104 of television 102 has a field of detection 106 for detecting a user 108 and food 110 that user 108 is eating. Television 102 may perform the implementations described herein alone or in combination with other devices.

For ease of illustration, FIG. 1 shows one block for each of television 102 and device 104. Blocks 102 and 104 may represent appliances and devices. In other implementations, environment 100 may not have all of the components shown and/or may have other elements including other types of elements instead of, or in addition to, those shown herein. For example, television 102 may include integrated and/or remote sensors (or sensor arrays) including remote controller(s), microphones, cameras and other sensors to monitor, detect and track a user's behavior/activity. As described in more detail herein, the system identifies and prevents health problems. The system detects problems earlier and reliably without the user needing to wear or carry an electronic device.

Figure 2:
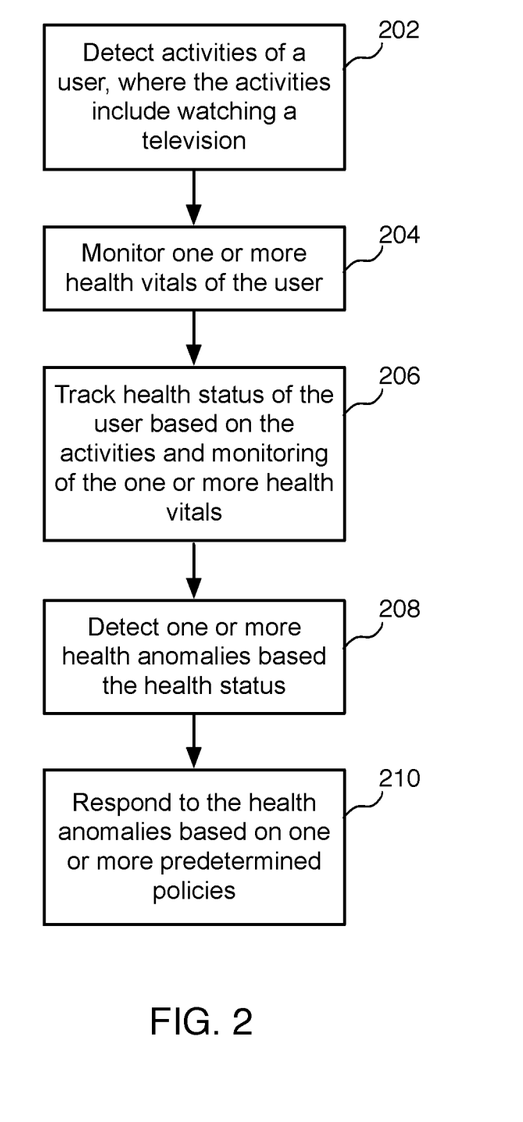
FIG. 2 illustrates an example flow diagram for monitoring the health condition of a television user, according to some implementations.

FIG. 2 illustrates an example flow diagram for monitoring the health condition of a television user, according to some implementations. As described in more detail herein, a system automatically tracks a user's health status and trends while the user is watching television. Referring to both FIGS. 1 and 2, a method is initiated at block 202, where the system such as television 102 detects one or more activities of a user. In various implementations, the system is in a fixed location. For example, the system is associated with a television.

As described in more detail herein, the one or more activities include watching television. For example, in some implementations, the system may detect when the user is in a stationary position in front of the television. In some implementations, the system may continue to detect information from the user even if the user is not watching television. The system may continue to operate even if the television is in standby mode. For example, the system may track if the user is relaxing without watching television.

In various implementations, the one or more activities include eating. In various implementations, the system recognizes a type of food that the user is eating. Example implementations directed to food are described in more detail herein.

In various implementations, the one or more activities include exercise. For example, system may detect when the user exercising in front of the TV. In some implementations, the system may detect that the user is exercises based on pattern recognition. For example, the system may detect repetitive motion such as calisthenics (e.g., push ups, crunches, using exercise equipment, yoga, etc.). Many users follow workout videos or use exercise equipment while they watch TV.

At block 204, the system monitors one or more health vitals of the user. In various implementations, the system performs the monitoring of the one or more health vitals by/via a television remote control. Example implementations directed to monitoring health vitals utilizing a television remote control are described in more detail herein. In various implementations, at least one of the health vitals is heart rate.

In some implementations, the system may utilize a built-in or external microphone to sense changes (from norm) in voice, breathing, sleeping, pattern, snoring, etc. This may be achieved with or without a camera. In various implementations, the microphone may be integrated with a TV remote control or speaker system.

At block 206, the system tracks the health status of the user based on the one or more activities and based on the monitoring of the one or more health vitals. For example, the system may record audio and use data analysis locally or in the cloud to detect who is in the room, biometric sleeping rhythms, and/or motion patterns in order to detect the health status of the user. In some implementations, the system may also utilize a built in or Wi-Fi connected camera to capture infrared video. The system may use the video to track motion patterns in order to detect how active the user is (e.g., how much the user is eating, moving, etc.).

At block 208, the system detects one or more health anomalies based the health status. In various implementations, the system determines and analyzes behavior patterns over time in order to build baselines. The system may then compare current data to the baselines in order to identify worsening trends or key signals that may indicate a health problem.

At block 210, the system responds to the one or more health anomalies based on one more predetermined policies. For example, in some implementations, the system may display data patterns, including health anomalies, to the user or may share data patterns with authorized caregivers and/or family members.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

Figure 3:
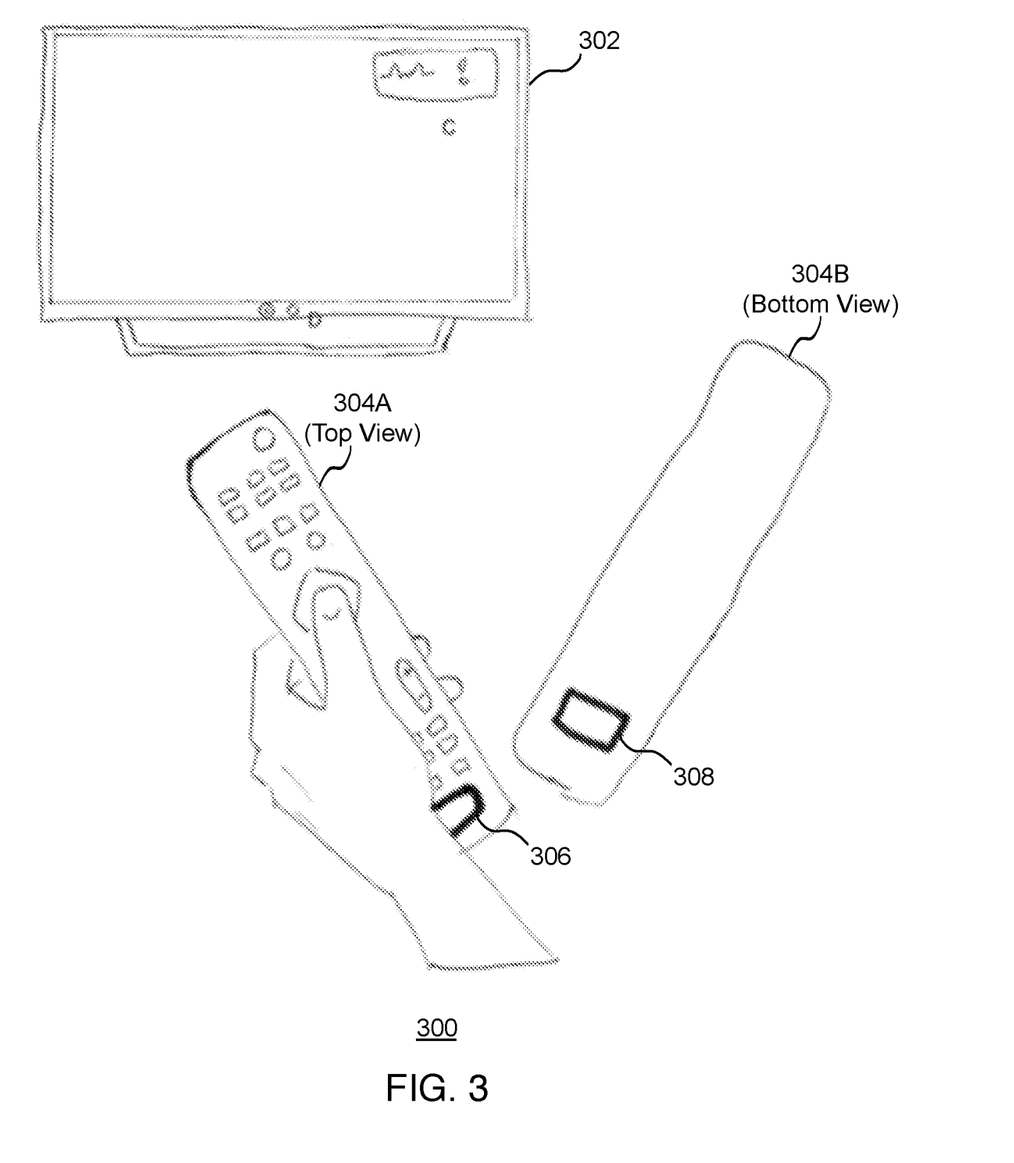
FIG. 3 illustrates a block diagram of an example television environment, which may be used for some implementations described herein.

FIG. 3 illustrates a block diagram of an example television environment 300, which may be used for some implementations described herein. Shown is a television 302 and a remote control 304 with a top view 304A and a bottom view 304B. Also shown are biometric sensors 306 and 308 in remote control 304. In some implementations, when remote control 304 is held by the user, one or more of biometric sensors 306 and 308 senses the signature of the user (relative to a previous established bio-metric register) and calibrates differences from its norm to infer various health conditions. For example, a biometric sensor may detect the heart rate, galvanic skin response (GSR), and fingerprint of the user and detect anomalies in the heart rate.

In some implementations, biometric sensors 306 and 308 may passively track heart rate and GSR data when the remote is being cradled in the user's hand. Biometric sensor 306 on the front of the remote may be used to take active, more detailed heart rate measurements when the user places his or her finger on the front of the phone. At the same time, a built-in camera may capture emotion, facial expressions, pupillary response, and capillary response in the face, as well as matching data collected to specific people with facial recognition. The built-in microphone may track breathing rate and types of breath. The system aggregates this data. The system may use an algorithm with machine learning to scan the data, establish a baseline for each person (based on facial recognition from the camera), and create events for deviations from the norm.

In some implementations, user identification may be established using a camera and facial recognition and/or using a microphone and speech recognition. This allows for passive tracking of galvanic skin response or conductance (GSR), heart rate, and flush patterns in the face, pupil dilation, breathing patterns, and other health conditions. In some implementations, the system may also be used to monitor and serve personalized content by pairing specific television content with positive emotional responses detected by the biometric sensors. The system may also use fingerprint sensing to control access to television content, which could serve as a replacement for a parental lock personal identification number.

Figure 4:
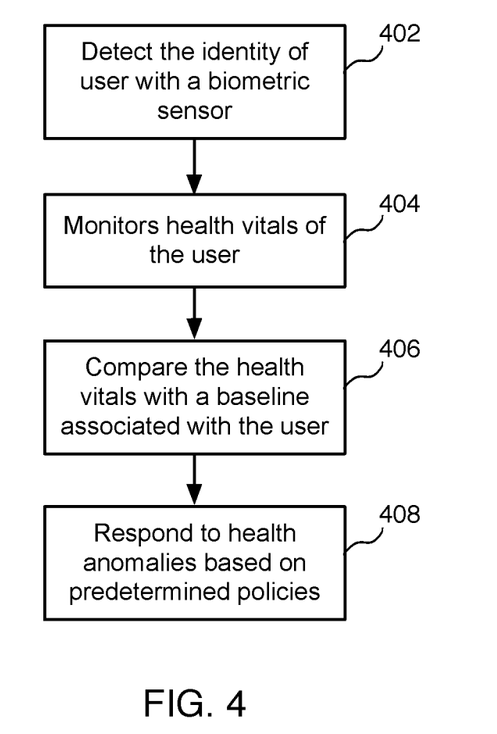
FIG. 4 illustrates an example flow diagram for monitoring the health condition of a television user using a biometric sensor, according to some implementations.

FIG. 4 illustrates an example flow diagram for monitoring the health condition of a television user using a biometric sensor, according to some implementations. As described in more detail herein, implementations detect the identity of the user and the health condition of the user by using one or more biometric sensors in a remote control for a television. Referring to both FIGS. 3 and 4, a method is initiated at block 402, where the system detects the identity of user with a biometric sensor.

At block 404, the system monitors one or more health vitals of the user. As described in more detail herein, the system may monitor heath vitals using devices such as a television remote control with one or more integrated biometric sensors. The particular device or devices may vary depending on the particular implementation. For example, in some implementations, the system may communicate with body-worn sensors in order to augment any passively collected data.

At block 406, the system compares the one or more health vitals with a baseline associated with the user. In some implementations, the system may aggregate health vital data from one or more sensors from one or more devices, and compare the data with the user baseline. In various implementations, system may compare multiple health vitals with multiple corresponding baselines (e.g., heart rate, blood pressure, sugar levels, etc.). The particular baselines may vary, depending on the particular implementation.

At block 408, the system responds to one or more health anomalies based on one more predetermined policies. The system tracks patterns and alerts the user to any problematic health states they may be experiencing, or can help them manage healthier habits (such as requiring exercise for children to continue watching specific content). The system may publish this information as a health report for each predetermined person, and may also be pushed to the user as notifications for more critical issues or to modify behavior.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

Figure 5:
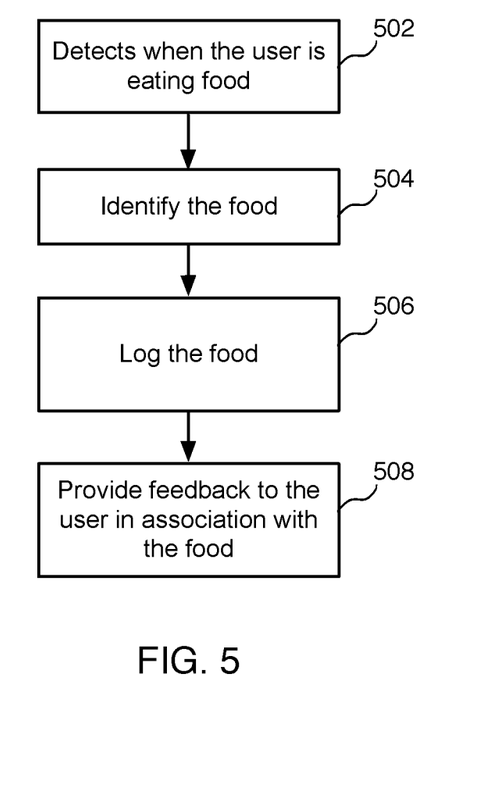
FIG. 5 illustrates an example flow diagram for monitoring food consumption of a television user, according to some implementations.

FIG. 5 illustrates an example flow diagram for monitoring food consumption of a television user, according to some implementations. As described in more detail herein, implementations perform food identification and logging of food consumption of a user. Referring to both FIGS. 1 and 5, a method is initiated at block 502, where the system detects when the user is eating food. For example, the user may be eating while watching TV. The system may utilize a TV-mounted camera or other camera aimed at the user to detect when the user is eating food, as well as to identify the user by facial recognition. In some implementations, the system may use pattern recognition to identify eating activity. In some implementations, the system may also monitor and log the speed of eating, chewing habits, and posture.

At block 504, where the system identifies the food. In some implementations, the system may identify the food using one or more cameras and image recognition. The system captures patterned recognized food that is eaten and the amount eaten, and the system calculates caloric content. In some implementations, the system may determine other information such as nutrition by referencing an appropriate food database. In some implementations, the system enables the user to correct inaccurately recognized foods. For example, the system may identify a particular food and ask the user to confirm if the food is correctly identified. The system may also provide a user interface for the user to review a list of identified foods and confirm if the foods are correctly identified, which can be done at a later time.

In some implementations, volume may be calculated by comparing the size or amount of food with a known object (e.g., the plate, the user's hand, etc.). Alternatively, two cameras may be used for volume estimation. The system may access to a comprehensive food database and advanced image recognition technology to accurately recognize and calculate the nutrition values of each dish. The system may also access other food-related information such as recipes that the user has requested in the past in order to make the analysis more accurate.

At block 506, the system logs the food. The system may log the food that is recognized by image recognition techniques. The system automatically records and tracks the food being eaten. This eliminates the need for the user to actively log food. The user need not manually log his or her food consumption, possibly biasing the data collection with subjective input as to the amounts or time of consumption. The user's food consumption is tracked objectively.

At block 508, the system provides feedback to the user in association with the food. This enables the user to monitor his or her food consumption in order to lose weight or control and monitor food for other health reasons. For example, some people might eat too much which watching TV. The system may notify or suggest to the user to be aware of how much the user is eating.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

Figure 6:
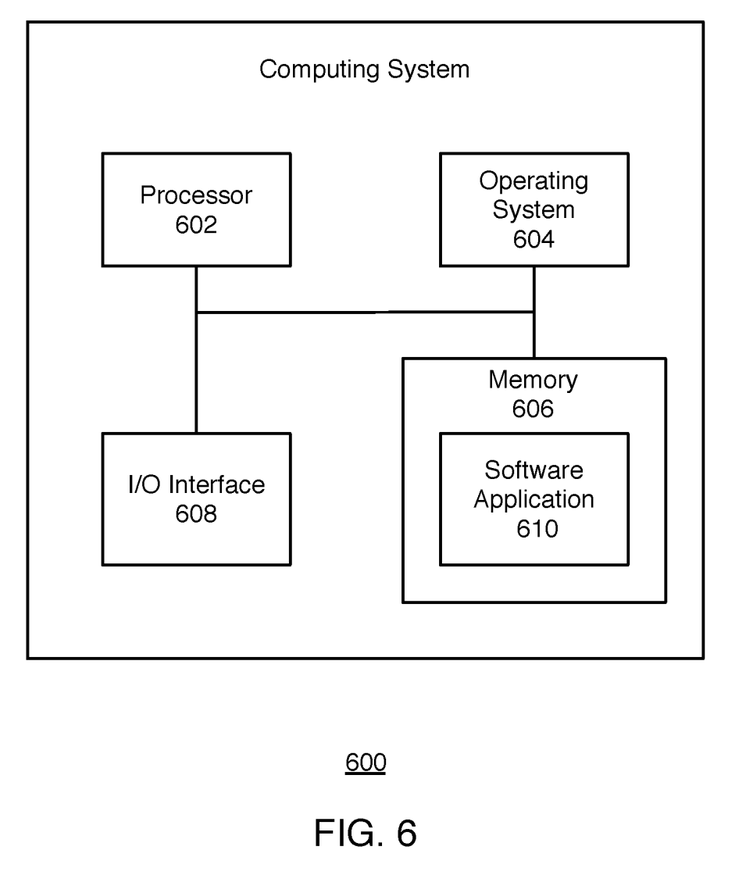
FIG. 6 illustrates a block diagram of an example computing system, which may be used for some implementations described herein.

FIG. 6 illustrates a block diagram of an example computing system 600, which may be used for some implementations described herein. For example, computing system 600 may be used to implement television 102 of FIG. 1, as well as to perform implementations described herein. In some implementations, computing system 600 may include a processor 602, an operating system 604, a memory 606, and an input/output (I/O) interface 608. In various implementations, processor 602 may be used to implement various functions and features described herein, as well as to perform the method implementations described herein. While processor 602 is described as performing implementations described herein, any suitable component or combination of components of computing system 600 or any suitable processor or processors associated with computing system 600 or any suitable system may perform the steps described. Implementations described herein may be carried out on a user device, on a server, or a combination of both.

Computing system 600 also includes a software application 610, which may be stored on memory 606 or on any other suitable storage location or computer-readable medium. Software application 610 provides instructions that enable processor 602 to perform the implementations described herein and other functions. Software application may also include an engine such as a network engine for performing various functions associated with one or more networks and network communications. The components of computing system 600 may be implemented by one or more processors or any combination of hardware devices, as well as any combination of hardware, software, firmware, etc.

For ease of illustration, FIG. 6 shows one block for each of processor 602, operating system 604, memory 606, I/O interface 608, and software application 610. These blocks 602, 604, 606, 608, and 610 may represent multiple processors, operating systems, memories, I/O interfaces, and software applications. In various implementations, computing system 600 may not have all of the components shown and/or may have other elements including other types of components instead of, or in addition to, those shown herein.

Although the description has been described with respect to particular embodiments thereof, these particular embodiments are merely illustrative, and not restrictive. Concepts illustrated in the examples may be applied to other examples and implementations.

In various implementations, software is encoded in one or more non-transitory computer-readable media for execution by one or more processors. The software when executed by one or more processors is operable to perform the implementations described herein and other functions.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a non-transitory computer-readable storage medium (also referred to as a machine-readable storage medium) for use by or in connection with the instruction execution system, apparatus, or device. Particular embodiments can be implemented in the form of control logic in software or hardware or a combination of both. The control logic when executed by one or more processors is operable to perform the implementations described herein and other functions. For example, a tangible medium such as a hardware storage device can be used to store the control logic, which can include executable instructions.

Particular embodiments may be implemented by using a programmable general purpose digital computer, and/or by using application specific integrated circuits, programmable logic devices, field programmable gate arrays, optical, chemical, biological, quantum or nanoengineered systems, components and mechanisms. In general, the functions of particular embodiments can be achieved by any means as is known in the art. Distributed, networked systems, components, and/or circuits can be used. Communication, or transfer, of data may be wired, wireless, or by any other means.

A "processor" may include any suitable hardware and/or software system, mechanism, or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems. A computer may be any processor in communication with a memory. The memory may be any suitable data storage, memory and/or non-transitory computer-readable storage medium, including electronic storage devices such as random-access memory (RAM), read-only memory (ROM), magnetic storage device (hard disk drive or the like), flash, optical storage device (CD, DVD or the like), magnetic or optical disk, or other tangible media suitable for storing instructions (e.g., program or software instructions) for execution by the processor. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system).

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

What is claimed is:

1. A system comprising:
   one or more processors; and
   logic encoded in one or more non-transitory computer-readable storage media for execution by the one or more processors and when executed operable to perform operations comprising:
   identifying a user using facial recognition and machine learning;
   detecting one or more activities of the user, wherein the one or more activities include watching a television and eating while watching the television;
   recognizing each type of food using one or more cameras, image recognition, and a food database;
   logging each type of food, an amount of each type of food, and a time that each type of food was consumed while the user is watching the television;
   monitoring, using a one or more sensors, one or more health vitals of the user using machine learning to scan the one or more health vitals, and wherein the monitoring of the one or more health vitals is performed in association with a television remote control;

tracking a health status of the user based on the one or more activities and based on the monitoring of the one or more health vitals;

detecting one or more health anomalies based the health status;

responding to the one or more health anomalies using machine learning and based on one or more predetermined policies; and providing feedback to the user on a display device in association with the food, wherein the feedback comprises the amount of food that the user is eating while watching the television.

2. The system of claim 1, wherein the system is in a fixed location.

3. The system of claim 1, wherein the system is associated with the television.

4. The system of claim 1, wherein the logic when executed is further operable to perform operations comprising monitoring the one or more heath vitals using the television remote control with one or more integrated biometric sensors.

5. The system of claim 1, wherein the monitoring of the one or more health vitals is performed in association with a television remote control.

6. The system of claim 1, wherein at least one of the health vitals is heart rate.

7. A non-transitory computer-readable storage medium with program instructions stored thereon, the program instructions when executed by one or more processors are operable to perform operations comprising:

identifying a user using facial recognition and machine learning;

detecting one or more activities of the user, wherein the one or more activities include watching a television and eating while watching the television;

recognizing each type of food using one or more cameras, image recognition, and a food database;

logging each type of food, an amount of each type of food, and a time that each type of food was consumed while the user is watching the television;

monitoring, using a one or more sensors, one or more health vitals of the user using machine learning to scan the one or more health vitals, and wherein the monitoring of the one or more health vitals is performed in association with a television remote control;

tracking a health status of the user based on the one or more activities and based on the monitoring of the one or more health vitals;

detecting one or more health anomalies based the health status;

responding to the one or more health anomalies using machine learning and based on one or more predetermined policies; and providing feedback to the user on a display device in association with the food, wherein the feedback comprises the amount of food that the user is eating while watching the television.

8. The computer-readable storage medium of claim 7, wherein the computer-readable storage medium is in a fixed location.

9. The computer-readable storage medium of claim 7, wherein the instructions are performed in association with the television.

10. The computer-readable storage medium of claim 7, wherein the instructions when executed are further operable to perform operations comprising monitoring the one or more heath vitals using the television remote control with one or more integrated biometric sensors.

11. The computer-readable storage medium of claim 7, wherein the monitoring of the one or more health vitals is performed in association with a television remote control.

12. The computer-readable storage medium of claim 7, wherein at least one of the health vitals is heart rate.

13. A computer-implemented method comprising:

identifying a user using facial recognition and machine learning;

detecting one or more activities of the user, wherein the one or more activities include watching a television and eating while watching the television;

recognizing each type of food using one or more cameras, image recognition, and a food database;

logging each type of food, an amount of each type of food, and a time that each type of food was consumed while the user is watching the television;

monitoring, using a one or more sensors, one or more health vitals of the user using machine learning to scan the one or more health vitals, and wherein the monitoring of the one or more health vitals is performed in association with a television remote control;

tracking a health status of the user based on the one or more activities and based on the monitoring of the one or more health vitals;

detecting one or more health anomalies based the health status;

responding to the one or more health anomalies using machine learning and based on one or more predetermined policies; and providing feedback to the user on a display device in association with the food, wherein the feedback comprises the amount of food that the user is eating while watching the television.

14. The method of claim 13, wherein a system implementing the method is in a fixed location.

15. The method of claim 13, wherein the method is performed in association with the television.

16. The method of claim 13, further comprising monitoring the one or more heath vitals using the television remote control with one or more integrated biometric sensors.

17. The method of claim 13, wherein the monitoring of the one or more health vitals is performed in association with a television remote control.

* * * * *